United States Patent
Galdonik et al.

(10) Patent No.: US 8,114,102 B2
(45) Date of Patent: Feb. 14, 2012

(54) TEMPORARY HEMOSTATIC PLUG APPARATUS AND METHOD OF USE

(75) Inventors: Jason A. Galdonik, Hanover, MN (US); Gregory Alan Boldenow, St. Michaels, MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 0 days.

(21) Appl. No.: 10/870,270

(22) Filed: Jun. 16, 2004

(65) Prior Publication Data
US 2005/0033361 A1     Feb. 10, 2005

Related U.S. Application Data

(60) Provisional application No. 60/479,216, filed on Jun. 16, 2003.

(51) Int. Cl.
    *A61B 17/08*        (2006.01)
(52) U.S. Cl. .................................. 606/153; 606/151
(58) Field of Classification Search ............. 606/157, 606/158, 153, 210, 151, 191, 198, 200, 213, 606/215–217; 294/99.1, 99.2, 118
    See application file for complete search history.

(56) References Cited

U.S. PATENT DOCUMENTS

| | | | |
|---|---|---|---|
| 3,221,746 A | 12/1965 | Noble | 606/151 |
| 3,265,069 A * | 8/1966 | Healey, Jr. et. al. | 606/153 |
| 3,391,690 A * | 7/1968 | Armao | 600/564 |
| 3,657,744 A | 4/1972 | Ersek | 606/153 |
| 4,083,162 A | 4/1978 | Regan et al. | 52/699 |
| 4,214,587 A | 7/1980 | Sakura, Jr. | 128/334 R |
| 4,368,736 A | 1/1983 | Kaster | 128/334 C |
| 4,485,816 A | 12/1984 | Krumme | 128/334 R |
| 4,503,569 A | 3/1985 | Dotter | 3/1.4 |
| 4,592,754 A | 6/1986 | Gupte et al. | 623/1 |
| 4,617,932 A | 10/1986 | Kornberg | 128/334 R |
| 4,624,255 A * | 11/1986 | Schenck et al. | 606/155 |
| 4,665,906 A | 5/1987 | Jervis | 128/92 YN |
| 4,733,665 A | 3/1988 | Palmaz | 128/343 |
| 4,739,762 A | 4/1988 | Palmaz | 128/343 |
| 4,787,899 A | 11/1988 | Lazarus | 623/1 |
| 5,041,082 A | 8/1991 | Shiber | 604/22 |
| 5,104,399 A | 4/1992 | Lazarus | 623/1 |
| 5,122,156 A | 6/1992 | Granger et al. | 606/219 |
| 5,135,467 A | 8/1992 | Citron | 600/16 |
| 5,147,370 A | 9/1992 | McNamara et al. | 606/108 |
| 5,207,695 A | 5/1993 | Trout, III | 606/153 |
| 5,211,658 A | 5/1993 | Clouse | 623/1 |
| 5,211,683 A | 5/1993 | Maginot | 128/898 |

(Continued)

FOREIGN PATENT DOCUMENTS

AU         670239        1/1994

(Continued)

*Primary Examiner* — Tuan Nguyen
(74) *Attorney, Agent, or Firm* — Lerner, David, Littenberg, Krumholz & Mentlik, LLP (57) ABSTRACT

A temporary hemostatic plug apparatus for use in a patient includes a plug structure configured to be placed within a patient's tubular body structure. The plug structure may be configured to be placed in an incision to create a bloodless operating field for a surgeon to operate, for example to perform an anastomosis. This may be done by deploying the plug structure out from within the lumen to create a hemostatic seal around the incision. Once the surgeon has completed the operation, the plug apparatus may be removed from the lumen through the incision, or through any other point of access in the lumen.

17 Claims, 9 Drawing Sheets

U.S. PATENT DOCUMENTS

| | | | |
|---|---|---|---|
| 5,234,447 A | 8/1993 | Kaster et al. | 606/153 |
| 5,275,622 A | 1/1994 | Lazarus et al. | 623/1 |
| 5,304,220 A | 4/1994 | Maginot | 623/1 |
| 5,316,023 A | 5/1994 | Palmaz et al. | 128/898 |
| 5,334,217 A | 8/1994 | Das | 606/213 |
| 5,354,309 A | 10/1994 | Schnepp-Pesch et al. | 606/198 |
| 5,354,336 A | 10/1994 | Kelman et al. | 623/6 |
| 5,360,443 A | 11/1994 | Barone et al. | 623/1 |
| 5,366,462 A | 11/1994 | Kaster et al. | 606/153 |
| 5,387,235 A | 2/1995 | Chuter | 623/1 |
| 5,391,159 A | 2/1995 | Hirsch et al. | 604/174 |
| 5,397,345 A | 3/1995 | Lazarus | 623/1 |
| 5,397,355 A | 3/1995 | Marin et al. | 623/12 |
| 5,433,727 A | 7/1995 | Sideris | 606/213 |
| 5,443,497 A | 8/1995 | Venbrux | 623/1 |
| 5,447,515 A * | 9/1995 | Robicsek | 606/158 |
| 5,452,733 A | 9/1995 | Sterman et al. | 128/898 |
| 5,456,712 A | 10/1995 | Maginot | 623/1 |
| 5,478,354 A | 12/1995 | Tovey et al. | 606/219 |
| 5,489,295 A | 2/1996 | Piplani et al. | 623/1 |
| 5,496,365 A | 3/1996 | Sgro | 623/1 |
| 5,507,769 A | 4/1996 | Marin et al. | 606/198 |
| 5,522,880 A | 6/1996 | Barone et al. | 623/1 |
| 5,522,882 A | 6/1996 | Gaterud et al. | 623/1 |
| 5,545,214 A | 8/1996 | Stevens | 623/2 |
| 5,562,728 A | 10/1996 | Lazarus et al. | 623/1 |
| 5,617,878 A | 4/1997 | Taheri | 128/898 |
| 5,618,311 A | 4/1997 | Gryskiewicz | 606/216 |
| 5,653,747 A | 8/1997 | Dereume | 623/1 |
| 5,676,670 A | 10/1997 | Kim | 606/108 |
| 5,681,336 A | 10/1997 | Clement et al. | 606/159 |
| 5,693,083 A | 12/1997 | Baker et al. | 623/1 |
| 5,695,504 A | 12/1997 | Gifford et al. | 606/153 |
| 5,702,412 A | 12/1997 | Popov et al. | 606/159 |
| 5,755,778 A | 5/1998 | Kleshinski | 623/1 |
| 5,833,698 A | 11/1998 | Hinchliffe et al. | 606/153 |
| 5,840,064 A | 11/1998 | Liprie | 604/96 |
| 5,843,164 A | 12/1998 | Frantzen et al. | 623/1 |
| 5,843,170 A | 12/1998 | Ahn | 623/1 |
| 5,843,175 A | 12/1998 | Frantzen | 623/1 |
| 5,853,419 A | 12/1998 | Imran | 606/191 |
| 5,853,422 A | 12/1998 | Huebsch et al. | 606/213 |
| 5,910,155 A | 6/1999 | Ratcliff et al. | 606/213 |
| 5,921,995 A | 7/1999 | Kleshinski | 606/153 |
| 5,922,022 A | 7/1999 | Nash et al. | 623/1 |
| 5,951,589 A | 9/1999 | Epstein et al. | |
| 5,976,159 A | 11/1999 | Bolduc et al. | 606/142 |
| 5,976,178 A | 11/1999 | Goldsteen et al. | 623/1 |
| 6,013,190 A | 1/2000 | Berg et al. | 216/34 |
| 6,026,814 A | 2/2000 | LaFontaine et al. | 128/898 |
| 6,035,856 A | 3/2000 | LaFontaine et al. | 128/898 |
| 6,036,702 A | 3/2000 | Bachinski et al. | 606/153 |
| 6,036,716 A | 3/2000 | Kruchinin et al. | 606/198 |
| 6,042,563 A * | 3/2000 | Morejohn et al. | 604/96.01 |
| 6,080,114 A * | 6/2000 | Russin | 600/567 |
| 6,113,612 A | 9/2000 | Swanson et al. | 606/153 |
| 6,120,432 A | 9/2000 | Sullivan et al. | 600/36 |
| 6,193,734 B1 | 2/2001 | Bolduc et al. | 606/153 |
| 6,248,121 B1 * | 6/2001 | Nobles | 606/194 |
| 6,464,709 B1 * | 10/2002 | Shennib et al. | 606/155 |
| 6,537,299 B1 * | 3/2003 | Hogendijk et al. | 606/213 |
| 6,620,177 B2 * | 9/2003 | Buelna et al. | 606/153 |
| 6,719,768 B1 * | 4/2004 | Cole et al. | 606/153 |
| 6,953,464 B2 * | 10/2005 | Buelna et al. | 606/153 |
| 2002/0019648 A1 | 2/2002 | Akerfeldt et al. | |
| 2002/0116019 A1 | 8/2002 | Buelna et al. | |

FOREIGN PATENT DOCUMENTS

| | | |
|---|---|---|
| DE | 28 22 603 A | 11/1979 |
| DE | 195 42 733 A | 7/1997 |
| DE | 29713335 | 10/1997 |
| EP | 539237 | 4/1993 |
| EP | 0 541 063 A | 5/1993 |
| EP | 0 541 063 A2 | 12/1993 |
| EP | 0 541 063 A3 | 12/1993 |
| EP | 637454 | 2/1995 |
| EP | 680734 | 11/1995 |
| EP | 684022 | 11/1995 |
| EP | 0 701 800 A1 | 3/1996 |
| EP | 0 712 614 A1 | 5/1996 |
| EP | 0 732 088 A2 | 9/1996 |
| EP | 0 732 089 A2 | 9/1996 |
| EP | 0 895 753 | 2/1999 |
| GB | 489316 | 7/1938 |
| GB | 2269104 A | 2/1994 |
| WO | WO 89/08433 A1 | 9/1989 |
| WO | WO 93/00868 | 1/1993 |
| WO | WO 93/13712 A | 7/1993 |
| WO | WO 93/20757 A2 | 10/1993 |
| WO | WO 94/01056 A1 | 1/1994 |
| WO | WO 95/21592 A1 | 8/1995 |
| WO | WO 95/32757 A1 | 12/1995 |
| WO | WO 96/01591 | 1/1996 |
| WO | WO 96/01599 | 1/1996 |
| WO | WO 96/14808 A1 | 5/1996 |
| WO | WO 96/18361 | 6/1996 |
| WO | WO 96/22745 | 8/1996 |
| WO | WO 96/25897 A2 | 8/1996 |
| WO | WO 97/13463 | 4/1997 |
| WO | WO 97/13471 | 4/1997 |
| WO | WO 97/27898 | 8/1997 |
| WO | WO 97/41779 A | 11/1997 |
| WO | WO 98/01086 | 1/1998 |
| WO | WO 98/02099 | 1/1998 |
| WO | WO 98/03118 | 1/1998 |
| WO | WO 98/07399 | 2/1998 |
| WO | WO 98/08462 A2 | 3/1998 |
| WO | WO 98/16161 | 4/1998 |
| WO | WO 98/19629 A2 | 5/1998 |
| WO | WO 98/19629 A3 | 5/1998 |
| WO | WO 98/19631 A1 | 5/1998 |
| WO | WO 98/26732 A1 | 6/1998 |
| WO | WO 98/27868 A | 7/1998 |
| WO | WO 98/38939 A1 | 9/1998 |
| WO | WO 98/38941 A1 | 9/1998 |
| WO | WO 98/38942 A1 | 9/1998 |
| WO | WO 98/42262 | 10/1998 |
| WO | WO 98/55027 A | 12/1998 |
| WO | WO 99/07289 A | 2/1999 |
| WO | WO 99/38454 | 8/1999 |

* cited by examiner

TEMPORARY HEMOSTATIC PLUG APPARATUS AND METHOD OF USE

This application claims the benefit of U.S. provisional patent application No. 60/479,216, filed Jun. 16, 2003, which is hereby incorporated by reference herein in its entirety.

BACKGROUND OF THE INVENTION

This invention relates to plugs for creating a fluid-less region in a tubular body structure in which a surgeon may operate. More particularly, this invention relates to temporary hemostatic plugs for creating a bloodless region in a blood vessel for operating on the blood vessel without the use of a side clamp or a connector. One situation in which this invention may be used is in coronary artery bypass graft (CABG) procedures. This invention may be used for bypass graft connections to the aorta.

A patient's weakened or diseased body organ tubing can often be repaired by replacing or supplementing the patient's existing natural body organ tubing with a graft structure. In CABG procedures, a surgeon may suture a graft to multiple locations along the coronary artery or between the aorta and a point on the coronary artery downstream from the blockage to bypass a blocked section. To proceed, a surgeon first makes an incision in the target vessel (e.g., artery, aorta, etc.), and then attaches the graft to the target vessel at the incision. A typical method for attaching the graft to the target vessel is by suture.

During this procedure, the surgeon may need to place a finger over the cored incision between the time that the cutter device is removed and the graft is sutured in place. In embodiments in which an anastomotic connector and delivery device is used, a finger may be used to obstruct the cored incision prior to deployment of the connector and graft. In particular, this may be very common when operating on the aorta. Sealing the incision with a finger may be very cumbersome and difficult for the surgeon. If the maneuver is not performed efficiently, patient blood loss may occur. Additionally, if the artery is subject to higher blood pressures, as is the aorta, "jetting" (e.g., spraying of blood through the incision) may occur. This phenomenon may further interfere with the procedure. Additionally, this phenomenon may be more readily experienced during "off-pump" CABG procedures.

To provide the surgeon with a clear operating field in which to suture, it is desirable to prevent blood from flowing around the incision. One method is to clamp off a portion of the artery where the graft will be made to create a bloodless region in which the surgeon may attach the graft. However, this clamping may dislodge plaques and other emboli, which may cause harm to the patient including, for example, adverse neurological effects, stroke, patient death, or other adverse health effects.

It is therefore an object of the present invention to provide apparatus and methods for creating a bloodless operating region for a surgeon during grafting procedures without using clamps or connectors.

SUMMARY OF THE INVENTION

In accordance with the present invention, apparatus and methods for creating a hemostatic seal between a surgical device and a lumen wall are provided. It should be understood that "lumen" may refer to a tubular body conduit, or to the cavity inside the tubular body conduit. Additionally, apparatus and methods for creating a bloodless operating field for a surgeon without using clamps or connectors are provided.

In one embodiment, a apparatus and method for providing a temporary hemostatic plug in a first incision in a lumen is provided. The apparatus and method may include a plug and a primary shaft connected to the plug. The plug may be placed in the lumen and positioned against the first incision to create a seal between the plug and the lumen. The plug may be inserted in the lumen through a second incision.

In another embodiment, a apparatus and method for providing a temporary hemostatic plug in an incision in a lumen to form a bloodless region for performing an operation is provided. The apparatus and method may include a plug and a primary shaft connected to the plug. The plug may be placed in the lumen and positioned against the incision to create a seal between the plug and the lumen. The outer surface of the plug may define a plug periphery such that the lumen is operated on outside the periphery.

In one embodiment, a apparatus and method for providing a temporary hemostatic plug in an incision in a lumen is provided. The apparatus and method may include a plug including a balloon, a shaft configured to be attached to the plug, and a tube configured to be concentrically slidable over the shaft to modify the shape of the balloon.

In yet another embodiment, a apparatus and method for providing a temporary hemostatic plug in a first incision in a lumen is provided. The apparatus and method may include a plug formed of a coil, a shaft connected to the distal end of the coil and a wire connected to the proximal end of the coil. The plug may be placed in the lumen and positioned against the incision to create a seal between the plug and the lumen, and the plug may be removed from the lumen by pulling on the wire to unwind the coil.

Further features of the invention, its nature and various advantages will be more apparent from the accompanying drawings and the following detailed description.

BRIEF DESCRIPTION OF THE DRAWINGS

FIG. 10b is a side-on view of the apparatus shown in FIG. 10a taken from line l0b-l0b in FIG. 10a.

FIG. 18b is a side-on view of the apparatus shown in FIG. 18a taken from line 18b-18b in FIG. 18a.

DETAILED DESCRIPTION OF THE PREFERRED EMBODIMENTS

Because the present invention has a number of different applications, each of which may warrant some modifications of such parameters as instrument size and shape, it is believed best to describe certain aspects of the invention with reference to simplified schematic drawings. To keep the discussion from becoming too abstract, however, and as an aid to better comprehension and appreciation of the invention, references will frequently be made to specific uses of the invention. Most often these references will be to use of the invention to provide a bloodless operating field using a temporary plug during a CABG procedure, and in particular providing a plug in the aorta or in the coronary artery during a bypass from the aorta to a point along the coronary artery which is downstream from the coronary artery narrowing. It is emphasized again, however, that this is only one of many possible applications of the invention.

Figure 1:
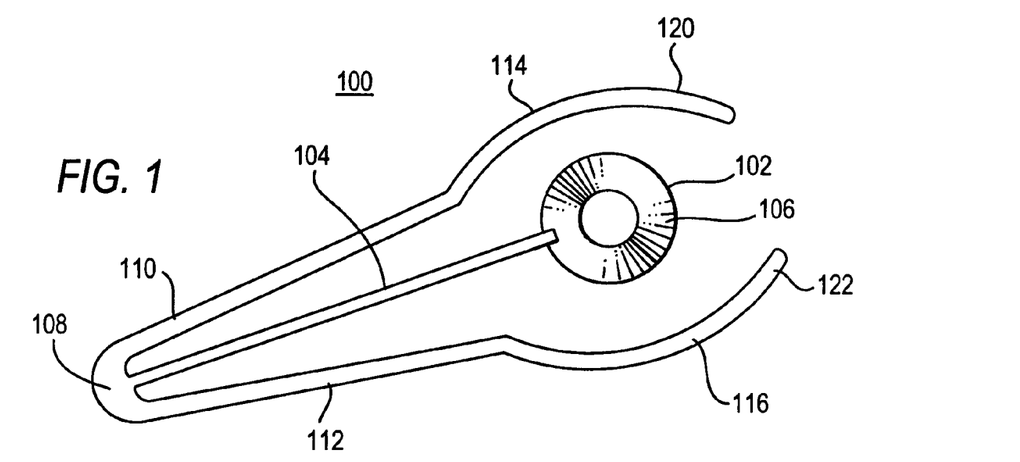
FIG. 1 is a perspective view of an illustrative embodiment of apparatus in accordance with the principles of the present invention.

FIG. 1 shows an embodiment of a plug apparatus according to the principles of the present invention. Plug apparatus 100 includes conical plug 102 mounted on shaft 104. Conical plug 102 may be rigid. In some embodiments, plug 102 may be made from a material with sufficient stiffness such that it may not be penetrated by a suture needle, such as plastic, metal, steel, or any other suitable material or combination of materials. In some embodiments, outer surface 106 of plug 102 may be coated with a surface treatment to increase strength, enhance lubricity, enhance hemostatic seal, or provide any other desirable property. The surface treatment, in conjunction with the conical shape, may help with guiding a suture through lumen wall 136 (shown in FIG. 2).

Plug apparatus 100 may also include side shafts 110 and 112 which may be rigidly connected to shaft 104 at proximal end 108, though plug apparatus 100 may also be used to seal incision 132 without side shafts 110 and 112. Side shafts 110 and 112 may include arms 114 and 116, respectively, which may be configured to assist plug 102 in achieving a hemostatic seal with a lumen wall. In some embodiments, shafts 104, 110 and 112 may be configured to be coplanar. In certain embodiments, shafts 104, 110 and 112 may not be straight shafts. Arms 114 and 116 may be coated with a surface treatment to increase friction. Alternatively, arms 114 and 116 may include a sheath of a high friction material such as, for example, a plastic or any other suitable material.

Shafts 104, 110 and 112 may be made from any material with suitable stiffness properties such as, for example, steel, hard plastic, a composite material, or any other suitable material. Shafts 104, 110 and 112 may be connected to each other by any suitable method such as, for example, welding, soldering, molding, a hinge, or any other suitable method.

Figure 2:
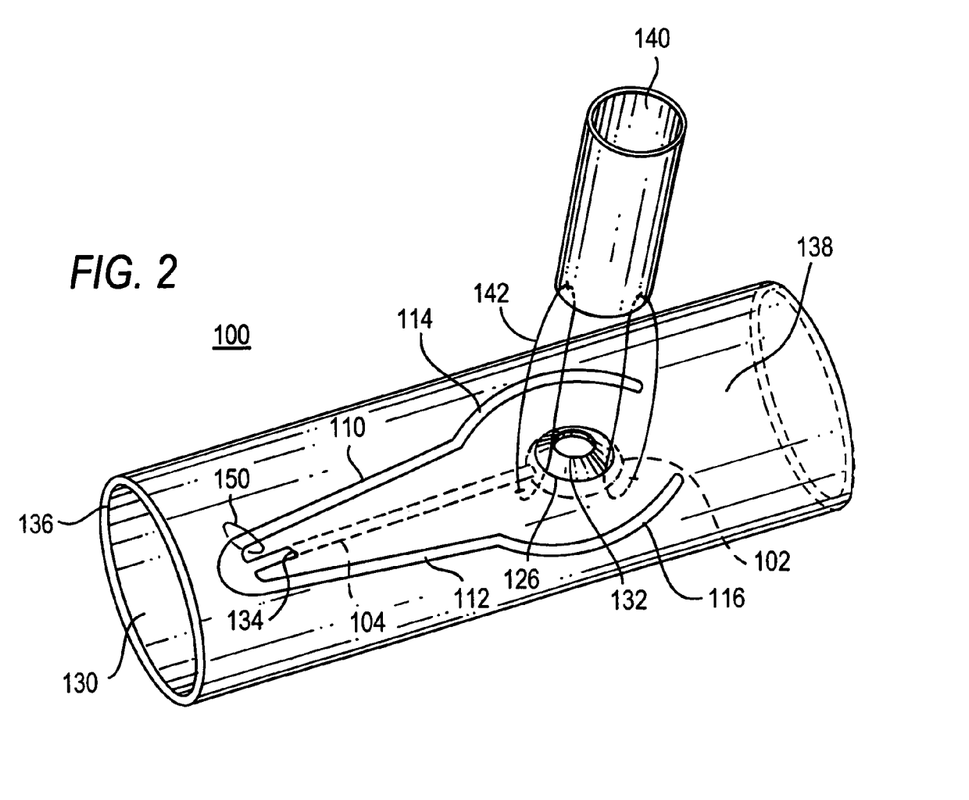
FIG. 2 is a perspective view of the apparatus of FIG. 1 in one stage of a related illustrative procedure in accordance with the principles of the present invention.

FIG. 2 shows plug apparatus 100 and tubular body conduit 138. Plug apparatus 100 is placed in lumen 130. It should be understood that the term "lumen" may refer to the cavity inside the tubular body conduit, or to the tubular body conduit itself. Shaft 104 and plug 102 may be inserted into lumen 130 through an opening made by the surgeon, such as incision 134. In one embodiment, a surgeon may place a purse string in lumen 130 and cut an opening such as incision 134 in the center of the purse string. Shaft 104 and plug 102 may then be introduced into lumen 130 through incision 134. The purse string may then be tightened around shaft 104 to prevent blood from leaking through incision 134. When positioned, plug 102 may be configured to be located in incision 132, and pressed into lumen wall 136 to create a seal. Plug 102 may be configured to have a diameter greater than the diameter of incision 132, which may be the incision the plug is configured to seal. Blood pressure in lumen 130 may press plug 102 against lumen wall 136 to assist in creating a hemostatic seal. The seal may be further enhanced by providing a downwards force into the lumen on shafts 110 and 112 and aR upwards force out of the lumen on shaft 104. Once a seal has been achieved, plug 102 may create a bloodless operating field for a surgeon around incision 132. As shown in FIG. 2, arms 114 and 116 of plug apparatus 100 are disposed in a plane and define a space therebetween. Arms 114 and 116 are adapted to press against an outer surface of lumen 130, i.e. lumen wall 136, in a use condition. In the use condition, when a hemostatic seal is created, plug 102 intersects the plane and a projection of plug 102 onto the plane from a direction normal to the plane is disposed entirely within the space.

Plug apparatus 100 may allow a surgeon to use standard surgical techniques to perform an anastomosis. In particular, a surgeon may scrape side 106 with a suture needle to ensure that all layers of lumen 130 are captured when attaching graft lumen 140 to lumen 130 at incision 132 with sutures 142. Outer surface 106 may define plug periphery 126 as the region where plug 102 is in contact with incision 132. Plug 102 may be configured such that the surgeon operates on the region of lumen 130 that is located outside periphery 126. This may allow the surgeon to take bites of lumen 130 as large as desired when performing the anastomosis. Also, this apparatus may allow a surgeon to perform 'reverse' bites where the needle is first inserted through lumen wall 136 and out incision 132 rather than first in through incision 132 and out lumen wall 136. The feature of operating outside the periphery of the plug may be included on any other suitable plug in accordance with the principles of the present invention.

In some embodiments, shafts 104, 110 and 112 may be attached to lumen 130 or to any other suitable portion of the operating field to hold plug 102 against incision 132. For example, proximal end 108 may be attached to lumen 130 by suture 150 or any other suitable mechanism. In one embodiment, holding proximal end 108 against lumen wall 136 may increase the pressure exerted by plug 102 against incision 132 and further prevent leaking.

Once sutures 142 have been placed between lumen 130 and graft lumen 140, sutures 142 may be cinched to pull graft lumen 140 over incision 132. Plug apparatus 100 may be removed through incision 134 before or after sutures 142 have been cinched.

It may be critical to limit the size of incision 134 both while inserting and removing plug apparatus 100, and in particular plug 102 in and from lumen 130. In some embodiments, plug 102 may be configured such that it may be constrained or dismantled. For example, plug 102 could be formed by thin-walled stainless steel structures, coils, thin-walled nitinol structures, or any other suitable material or structure. In particular, thin-walled structures may have a wall thickness in the range of 0.0005 to 0.0015 inches. A thin-walled structure may be collapsed, squashed, or pulled into a tube to be removed through an opening such as incision 134. A coil may be dismantled into its wire form to be removed through an opening such as incision 134. In other embodiments, plug 102 may change from a first, expanded configuration to a second, collapsed configuration. To ensure that plug 102 has sufficient strength to create a hemostatic seal when deployed in incision 132, apparatus 100 may include a balloon to provide support or to temporarily plug incision 132 while plug 102 is removed. Once plug 102 is removed, the balloon may be deflated and removed through incision 134.

Figure 3:
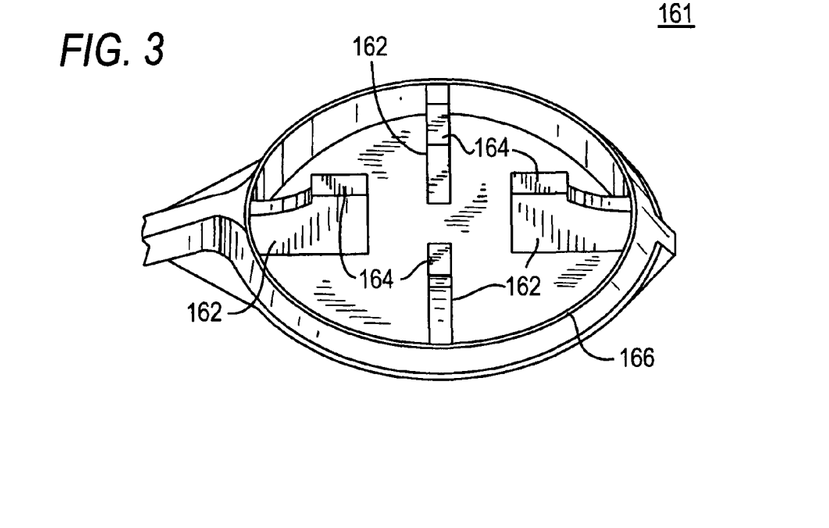
FIG. 3 is a perspective view of a portion of an illustrative embodiment of apparatus and a related illustrative procedure in accordance with the principles of the present invention.

FIG. 3 shows an illustrative alternative embodiment of the plug apparatus. In one embodiment, the top most portion of conical plug 161 may include a recessed level 160. Recessed level 160 may include any suitable number of ribs 162. In one embodiment, plug 161 may include four ribs. Ribs 162 may be configured to extend from recessed level 160 up to or beyond the top-most periphery 166 of plug 161.

Figure 4:
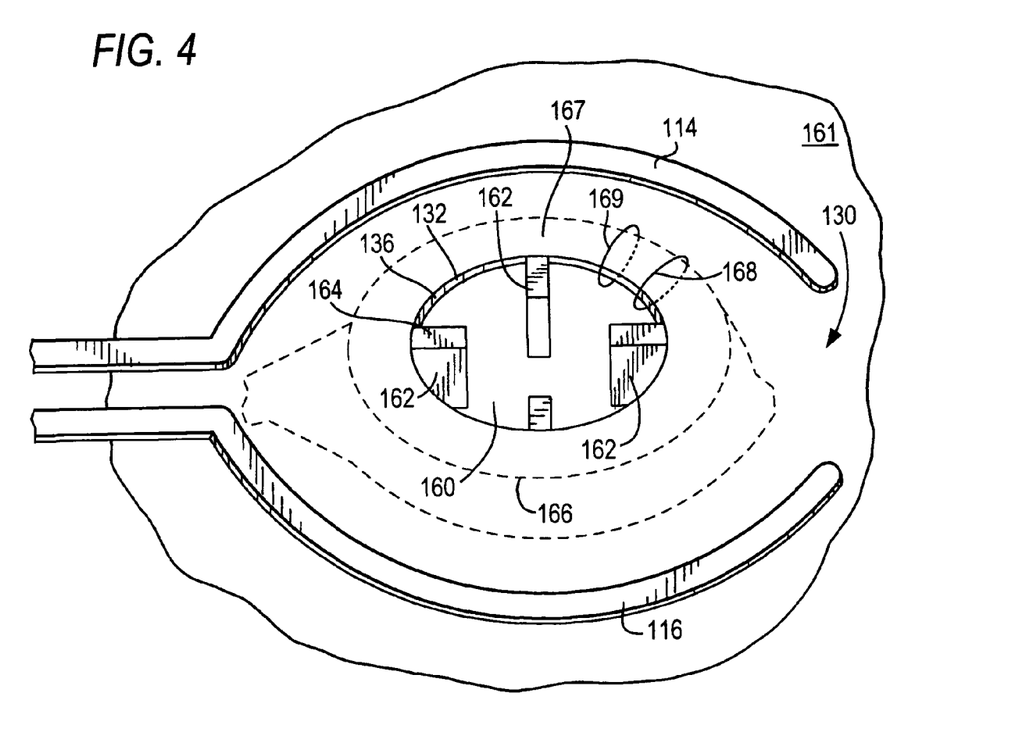
FIG. 4 is a view similar to FIG. 3 showing a portion of the illustrative procedure and related apparatus in accordance with the invention.

FIG. 4 shows a detailed view of plug 161 placed in lumen 130. Plug 161 is located underneath incision 132 such that outer periphery 166 extends beyond the periphery of incision 132. A hemostatic seal is provided by pushing plug 161 against lumen wall 136. Top-most periphery 166 may be configured to create a seal between lumen 130 and plug 161. In one embodiment, top-most periphery 166 may include a contour that is configured to match the inner contour of lumen wall 136. The contour may be configured to enhance the seal of plug 161 with lumen wall 136. A contoured structure may require less force to create a seal between plug 161 and lumen wall 136. Arms 114 and 116 may be configured to hold plug 161 against lumen wall 136 to maintain a seal. In one embodiment, top surface 164 may be configured such that lumen wall 136 rests on top surface 164 of ribs 162. Ribs 162 may be configured to extend far enough from periphery 166 towards the center of plug 161 to extend beyond incision 132. This configuration may allow a surgeon to see the full lumen wall 136, which may facilitate suturing.

Top-most periphery 166 may be configured to be placed against lumen wall 136 such that the lumen wall extends beyond periphery 166 and creates a ledge (e.g., overhang 167) which hangs over recessed level 160. The portion of the lumen that is operated on is the ledge, which is inside periphery 166.

Ribs 162 may provide the surgeon with visible access to the entire lumen wall, which may help prevent a tear in the inner lining of the lumen wall, such as aortic dissection in the case of the aorta. In particular, ribs 162 may help a surgeon capture the entire lumen wall thickness with a suture, as shown in FIG. 4, with suture 168. Suture 168 passes through the entire lumen wall thickness, including both the inner and outer layers. If the plug is smooth, the surgeon may have more difficulty capturing all of the lumen wall layers, and the suture may pass through only the outer layers of the lumen wall, as shown by suture 169. The suture does not capture the entire wall thickness, but only a portion of the wall, which may cause dissection.

Figure 5:
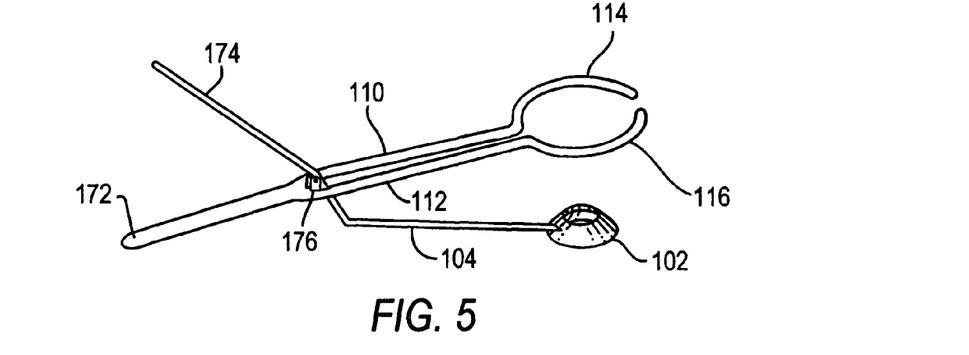
FIG. 5 is a perspective view of an illustrative embodiment of apparatus in accordance with the principles of the present invention.

FIG. 5 shows an alternate embodiment for the connection between shafts 110, 112 and 104. In some embodiments, shafts 110 and 112 may be connected to extension shaft 172, and shaft 104 may be connected to extension shaft 174. Shafts 110, 112 and 172 may form any suitable angle. Shafts 104 and 174 may form any suitable angle. In one embodiment, shafts 104 and 174 may form an angle configured to help a surgeon push plug 102 against a lumen wall. Shafts 172 and 174 may be coupled by any suitable hinge 176 including, for example, a pin, a living hinge, or any other suitable hinge. A living hinge may be formed by placing a more flexible piece of material between shafts 172 and 174, such as is found in DVD cases.

Figure 6:
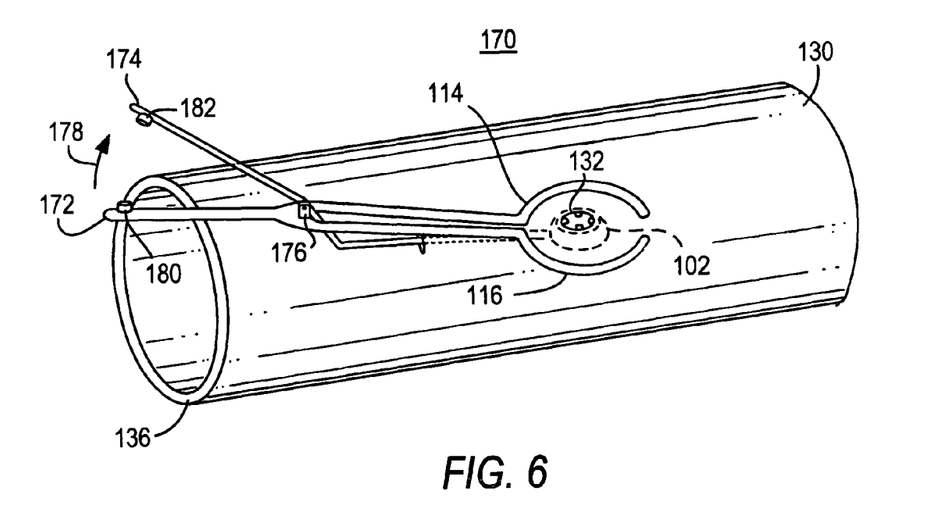
FIG. 6 is a view similar to FIG. 5 showing a portion of a particular illustrative procedure and related apparatus in accordance with the principles of the present invention.

FIG. 6 shows apparatus 170 inserted into lumen 130. To insert apparatus 170 into the lumen, shafts 110 and 112 may be positioned such that arms 114 and 116 are away from plug 102 and do not interfere with the placement of the plug within the lumen. For example, shaft 172 may be rotated with respect to shaft 174. Once plug 102 is properly placed in the lumen opposite incision 132, shaft 172 may be rotated with respect to shaft 174 such that arms 114 and 116 push against the lumen wall, increasing the pressure between plug 102 and the incision to create a hemostatic seal. Shafts 172 and 174 may have any configuration that may help create a hemostatic seal between plug 102 and the lumen. In the embodiment shown, shaft 172 may be moved in direction 178 to bring shaft 172 against shaft 174 and press arms 114 and 116 against lumen wall 136.

To hold shaft 172 against shaft 174, shaft 172 may include first locking portion 180 and shaft 174 may include second locking portion 182. First locking portion 180 may be configured to engage second locking portion 182 such that shafts 172 and 174 are held in a position such that arms 114 and 116 press against lumen wall 136.

Figure 7:
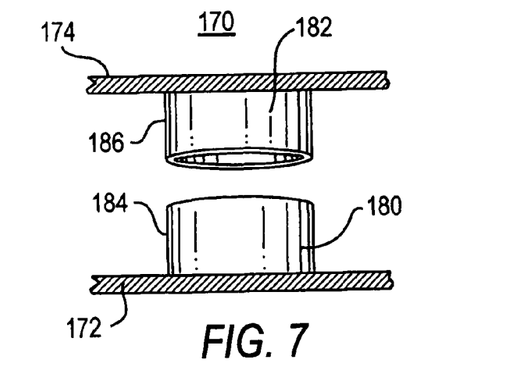
FIG. 7 is a perspective view of a portion of the illustrative procedure and related apparatus of FIG. 6 at a later stage of the procedure in accordance with the principles of the present invention.

First and second locking portions 180 and 182 may include magnets 184 and 186, as shown in FIG. 7. Magnetic portions 184 and 186 may be configured to attract each other such that shaft 172 is held against shaft 174 when magnetic portions 184 and 186 are in contact. Magnetic portions 184 and 186 may be a rare earth magnet, an electromagnet, a metal with suitable magnetic permeability, or any other suitable material. In one embodiment, magnetic portions 184 and 186 may be permanently fixed to shafts 172 and 174, respectively. In one embodiment, magnetic portions 184 and 186 may be removably fixed to shafts 172 and 174. Apparatus 170 may include a mechanism or device for separating magnetic portions 184 and 186 for removal of the apparatus.

Figure 8:
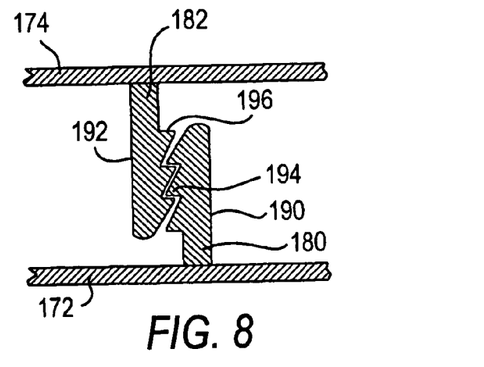
FIG. 8 is a perspective view of another embodiment of a portion of the illustrative procedure and related apparatus of FIG. 6 at a later stage of the procedure in accordance with the principles of the present invention.

FIG. 8 shows first and second locking portions 180 and 182 that include toothed protrusions 190 and 192. Protrusions 190 and 192 may be permanently fixed to shafts 172 and 174, respectively, and may be configured to extend away from their respective shafts, towards each other. Protrusions 190 and 192 may be configured to include any suitable number of teeth 194 and 196, respectively. When shaft 170 is approached to shaft 172, protrusions 190 and 192 may be configured to engage to hold shafts 170 and 172 together. In one embodiment, teeth 194 may be configured to engage teeth 196 to hold the shafts together. In one embodiment, protrusions 190 and 192 may include any suitable number of teeth. In particular, protrusions 190 and 192 may have more than one tooth each, which may allow multiple engagement positions for protrusions 190 and 192. Protrusions 190 and 192 may be similar to the protrusions of a hemostat.

Advantages of this apparatus include the possibility of accommodating any size suture 'bite.' In particular, since the suture needle is used on the outside of the plug, the size of the 'bite' is not limited by the size of an outer contour that is placed against the lumen wall. Plug 102 may have any suitable profile, and may have any suitable shape such as a cone, cone section, cube, sphere, hemisphere, or any other suitable shape. In particular, plug 102 may have a low profile, such as a small cone with a flat plate underneath. Additional advantages may include eliminating patient blood loss, eliminating the need to clamp lumen 130, prevention of leaving foreign material behind, minimization of compression force against lumen wall 136 to create a hemostatic seal, and the apparatus is adaptable with current surgical techniques, as well as other advantages. It will be understood that the features of plug 102 may be included in plug 161, and the features of plug 161 may be included in plug 102.

Figure 9:
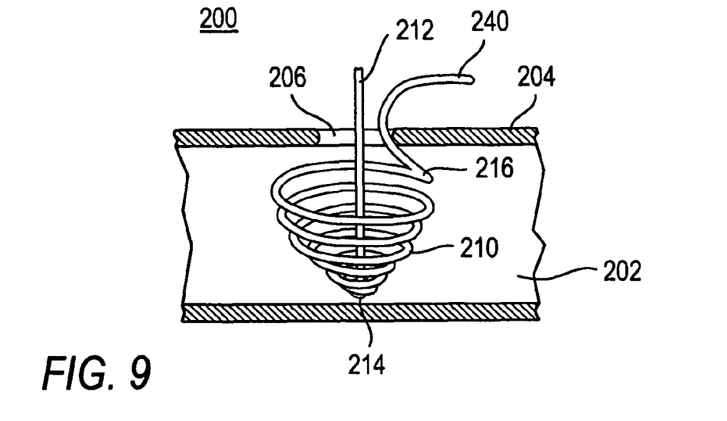
FIG. 9 is a simplified sectional view of a procedure and related apparatus in accordance with the principles of the present invention.

FIG. 9 shows another alternative embodiment according to the principles of the present invention. Plug apparatus 200 may be inserted into lumen 202 through incision 206. Plug apparatus 200 may include a plug 210 which may consist of a flexible strand 216 which may be molded into a conical shape to create a series of overlapping spirals. At the distal end 214 of plug 210, shaft 212 may be connected to the end of strand 216. In one embodiment, strand 216 may be made of any material with suitable elastic properties such as, for example, silicone, urethane, a low durometer material such as a polymer, a plastic, or any other suitable material. Shaft 212 may be configured to assist with the deployment and sealing of plug 210. In one embodiment, plug 210 is made of a material with sufficient stiffness that a suture needle may not penetrate the plug.

Figure 10A:
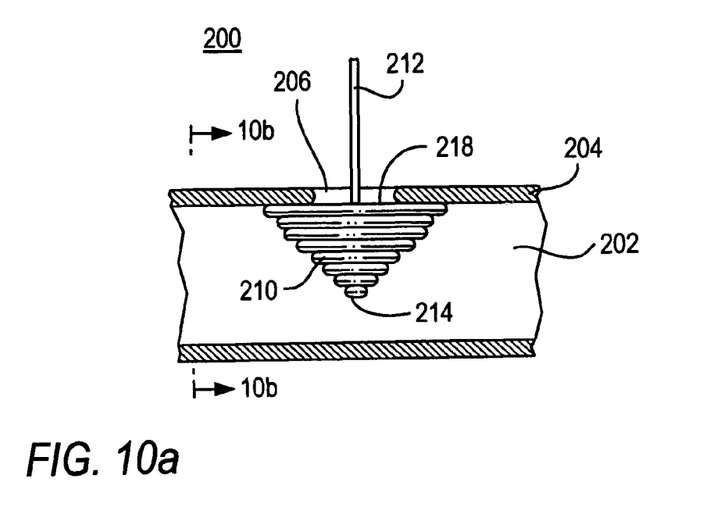
FIG. 10a is a simplified sectional view of the procedure and related apparatus of FIG. 9 in a later stage of the procedure in accordance with the present invention.

To deploy plug apparatus 200, shaft 212 is inserted into lumen 202 through incision 206. Flexible strand 216 may be compressed as it is inserted through incision 206. Once flexible strand 216 is entirely within lumen 202, shaft 212 may be pulled against lumen wall 204 to compress the overlapping spirals of plug 210, as shown in FIG. 10*a*. The top-most spiral of plug 210 may be compressed against lumen wall 204. Plug 210 may then create a seal between the top-most spiral and lumen wall 204, which may provide a bloodless operating field. The surgeon may operate within plug 210 without having any blood obscure the field. In one embodiment, shaft 212 may be attached by any suitable means to lumen 202 or any other suitable portion of the operating field such that plug 210 remains in contact with lumen wall 204 and provides a hemostatic seal.

Figure 10B:
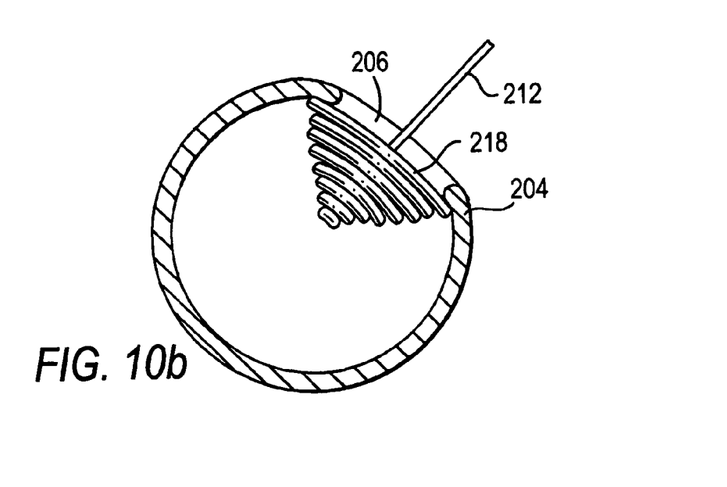

In one embodiment, the top-most spiral may include a contour 218 so that plug 210 more snuggly fits against curved lumen wall 204, as shown in FIG. 10*b*. Contour 218 may lower the required force on shaft 212 for a hemostatic seal between plug 210 and lumen wall 204. With a non-contoured device, more force must be applied to shaft 212 to flatten lumen wall 204 so that the top-most spiral and lumen wall 204 are in direct contact.

Figure 11:
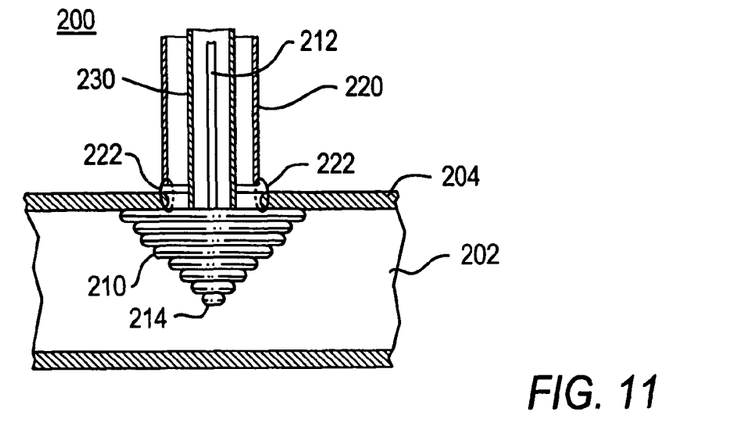
FIG. 11 is a simplified sectional view of the procedure and related apparatus of FIG. 10a in a still later stage of the procedure in accordance with the present invention.

To deploy plug apparatus 200 for some CABG procedures, shaft 212 and plug 210 may be placed within graft lumen 220, as shown in FIG. 11. In one embodiment, graft lumen 220 may be placed over shaft 212 before plug 210 is inserted into lumen 202 through incision 206. If plug apparatus 200 is deployed within graft lumen 220, shaft 212 may extend beyond the graft lumen so that the shaft may be pulled to create a proper hemostatic seal. Once graft lumen 220 is in place, a surgeon may suture the graft lumen onto lumen 202 using sutures 222. In one embodiment, sutures 222 may be cinched before removing plug apparatus 200.

To remove plug apparatus 200, tube 230 may be inserted over shaft 212. Tube 230 may be lowered to the anastomosis site. Once the tube in place, shaft 212 may be pulled through the tube, containing flexible strand 216 within the tube to prevent trauma to graft lumen 220. Tube 230 may be as small as possible, provided flexible strand 216 and shaft 212 fit through the tube. In some embodiments, it may be desirable to first remove the portion of flexible strand 216 that forms the top-most spiral, and remove the distal portion last. Wire 240 (FIG. 9) may be attached to the top-most portion of flexible strand 216, and may be used to pull flexible strand 216 out through tube 230.

Figure 12:
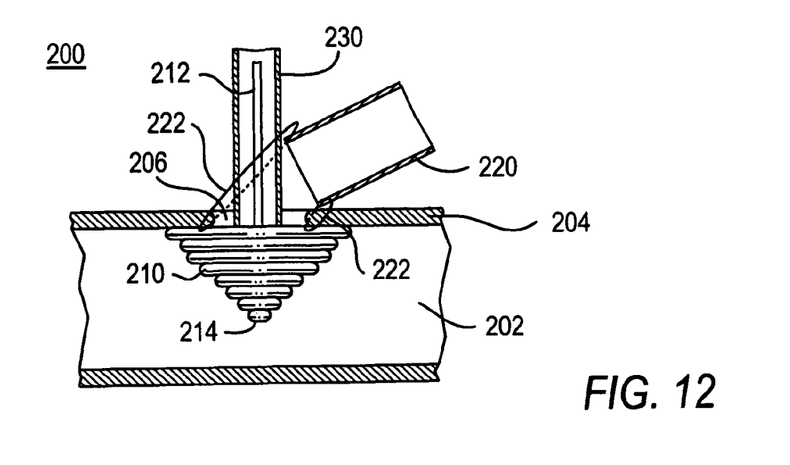
FIG. 12 is a simplified sectional view of the procedure and related apparatus of FIG. 10a in an alternate configuration of a still later stage of the procedure in accordance with the present invention.

In one embodiment, shaft 212 may be located outside graft lumen 220, and in between sutures 222. FIG. 12 shows graft lumen 220 attached to lumen 202 by sutures 222. Sutures 222 may remain uncinched until plug apparatus 200 is removed from lumen 202. Tube 230 may be lowered over shaft 212 until it is lowered to the anastomosis site. Once the tube is in place, shaft 212 may be pulled through the tube, containing flexible strand 216 within the tube to prevent trauma to graft lumen 220. Tube 230 may be as small as possible, provided flexible strand 216 and shaft 212 fit through the tube. In one embodiment, it may be desirable to first remove the portion of flexible strand 216 that forms the top-most spiral, and remove the distal portion last. A wire may be attached the that portion of flexible strand 216, and may be used to pull flexible strand out through tube 230.

Advantages of this apparatus include a soft atraumatic shaft which provides easy manipulation of plug 210. The over-lapping and unwinding spiral configuration aids in the introduction and removal of plug 210 through incision 206. The contoured shape of the top-most spiral enhances the hemostatic seal. Additional advantages may include eliminating patient blood loss, eliminating the need to clamp lumen 202, no foreign material left behind, minimization of compression force against lumen wall 204 to create a hemostatic seal, and the apparatus is adaptable with current surgical techniques, as well as other advantages.

Figure 13:
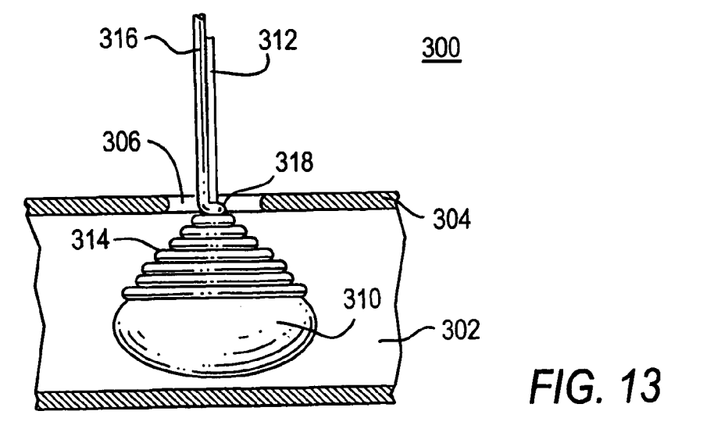
FIG. 13 is a simplified sectional view of an illustrative procedure and related apparatus in accordance with the present invention.

FIG. 13 shows an alternate plug apparatus according to the principles of the present invention. Plug apparatus 300 is inserted into lumen 302 through incision 306. Plug apparatus 300 includes balloon portion 310, tube 312, coil plug 314 and coil wire 316. In one embodiment, coil plug 314 may have a conical shape. Coil plug 314 may be made of any material with sufficient stiffness properties to prevent a suture needle from piercing the plug such as, for example, steel, plastic, silicone, urethane, a polymer, or any other suitable material. In one embodiment, coil plug 314 may be made from a material that has sufficient flexibility that the coil may be unwound. In one embodiment, coil plug 314 may be coated with a surface treatment to increase strength, enhance lubricity, enhance hemostatic seal, or any other desirable property. The conical shape may help with guiding a suture needle through lumen wall 304.

Wire 316 of coil plug 314 may extend beyond proximal portion 318 of the coil. Wire 316 may be configured to extend outside of lumen 302 when plug apparatus 300 is inserted into the lumen. In one embodiment, pulling on wire 316 may unwind coil plug 314 to allow the plug to be removed from within lumen 302. When wound, coil plug 314 may be configured to be located on top of balloon portion 310, which may be inflated to provide additional rigidity for coil plug 314. Balloon portion 310 may be inflated and deflated through tube 312. In one embodiment, wire 316 and tube 312 extend side by side from lumen 302.

To insert plug apparatus 300 into lumen 302 through incision 306, balloon 310 may be partially inflated. The partial inflation may create enough rigidity for the balloon to snap or pop into incision 306. In one embodiment, plug 314 may be pressed onto balloon portion 310 such that plug 314 also snaps into lumen 302. In another embodiment, plug 314 may be compressed to fit through incision 306 and expand once it is released. In one embodiment, balloon portion 310 may be shaped to ease the insertion of the balloon portion through incision 306.

Once inserted into lumen 302, balloon portion 310 may be fully inflated. Balloon portion 310 and coil plug 314 may be pulled up into lumen wall 304 by pulling on tube 312. A bloodless operating field may be created when plug 314 is pulled toward lumen wall 304 and a hemostatic seal has been created. In one embodiment, blood pressure inside lumen 302 may improve the seal by pressing plug 314 against lumen wall 304. The seal may be further improved by providing an appropriate force on plug 314, balloon 310, tube 312, or any other suitable portion of plug apparatus 300.

Figure 14:
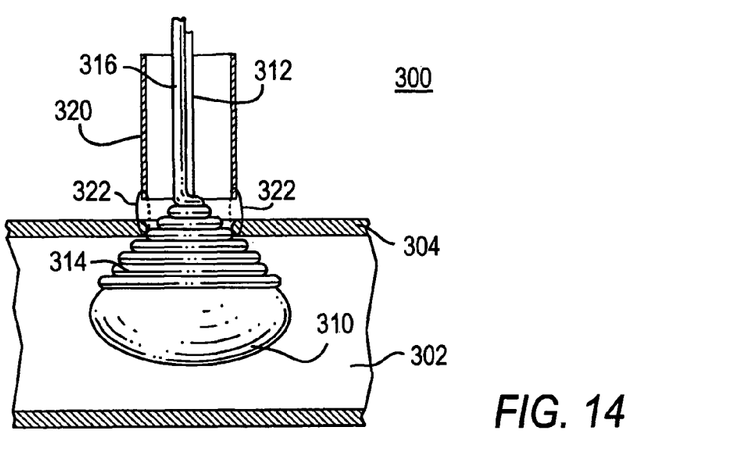
FIG. 14 is a simplified sectional view of the procedure and related apparatus of FIG. 13 in a later stage of the procedure in accordance with the present invention.

Once plug apparatus 300 is in place, a surgeon may suture graft lumen 320 to incision 306 with sutures 322. In one embodiment, tube 312 and wire 316 may be located inside graft lumen 320, as shown in FIG. 14. In another embodiment, plug apparatus 300 may be located outside of graft lumen 320, and may be located between sutures 322. Plug apparatus 300 may assist a surgeon in performing suitable surgical techniques to perform an anastomosis. In particular, a surgeon may scrape the side of coil plug 314 with a suture needle to ensure that all layers of lumen 302 are captured when attaching graft lumen 320 to lumen 302. Similar to plug 102 (FIG. 1), plug 314 may be configured such that the surgeon operates on the region of lumen 302 that is located outside the periphery of plug 314. Thus, the surgeon may take bites of lumen 230 as large as desired when performing the anastomosis. Plug apparatus 300 may allow a surgeon to perform 'regular' bites where the needle is first inserted through incision 306 and out lumen wall 304 as well as 'reverse' bites where the needle is first inserted through lumen wall 304 and out incision 306.

Figure 15:
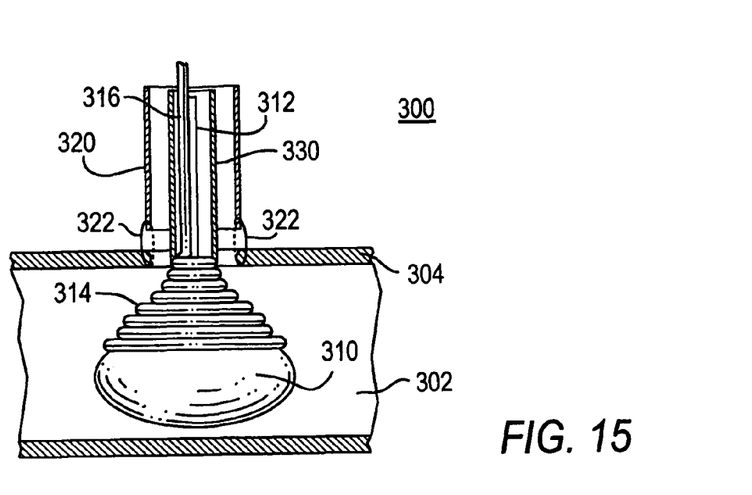
FIG. 15 is a simplified sectional view of the procedure and related apparatus of FIG. 14 in a still later stage of the procedure in accordance with the present invention.
Figure 16:
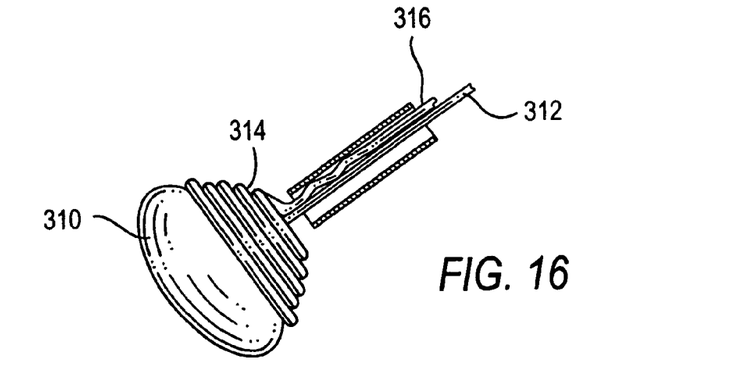
FIG. 16 is a simplified sectional view of a portion of the apparatus of FIG. 13 at a later stage of the procedure in accordance with the principles of the present invention.

To remove plug apparatus 300 from the anastomosis site, removal tube 330 is inserted over coil wire 316. FIG. 15 shows removal tube 330 inserted over both coil wire 316 and tube 312. In another embodiment, removal tube 330 may be inserted only over coil wire 316. Balloon portion 310 may be advanced away from incision 306 and the anastomosis to free lumen wall 304. Removal tube 330 may be advanced down wire 316 until it is placed tightly against the anastomosis. Wire 316 may then be pulled out of tube 330, unwinding coil plug 314 through the tube, as shown in FIG. 16. In one embodiment, tube 330 may have sufficient rigidity to prevent the wire of coil plug 314 from piercing tube 330 and causing trauma to the anastomosis. Once coil 314 has been removed from within lumen 302, balloon portion 310 may be deflated and removed as well. Tube 330 may be removed concurrently with coil plug 314 or with balloon portion 310. If tube 312, wire 316 and tube 330 are placed within graft lumen 320, sutures 322 may be cinched before removing plug apparatus 300 from lumen 302, provided that tube 312, wire 316 and tube 330 extend beyond the end of graft lumen 320. If tube 312, wire 316 and tube 330 are not placed within graft lumen 320, sutures 322 may remain loose as the different components of plug apparatus 300 may be removed in between sutures.

Advantages of this apparatus include the possibility of accommodating any size suture 'bite.' In particular, since the suture needle is used on the outside of the plug, the size of the 'bite' is not limited by the size of an outer contour that is placed against the lumen wall. The suture needle may easily slide along the outer surface of plug 314 to guide the needle during the suturing. The plug size may be easily matched to the size of incision 306 to provide an optimal seal with a low plug profile. Rigid coil plug 314 may prevent balloon portion 310 from being punctured by a suture needle. Since the coil can be unwound and the balloon deflated, plug apparatus 300 may be easily introduced into any suitable incision, and may be easily removed in between any sutures, even if partially cinched. Additional advantages may include eliminating patient blood loss, eliminating the need to clamp lumen 302, no foreign material left behind, minimization of compression force against lumen wall 304 to create a hemostatic seal, and the apparatus is adaptable with current surgical techniques, as well as other advantages.

Figure 17:
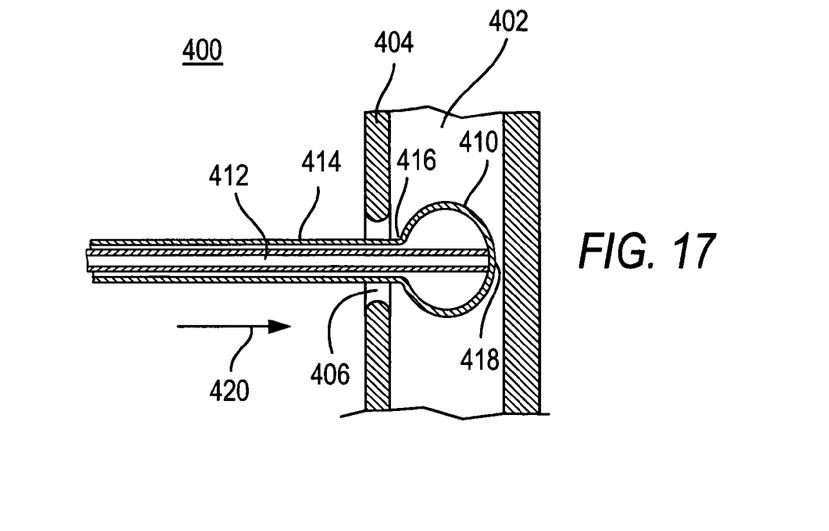
FIG. 17 is a simplified sectional view of an illustrative procedure and related apparatus in accordance with the present invention.

FIG. 17 shows one embodiment of a hemostatic plug apparatus in accordance with the present invention. Plug apparatus 400 is configured to be used in lumen 402. Lumen 402 may be the aorta, a coronary artery, or any other lumen in a patient that would need a temporary plug during an operation. Lumen 402 is defined by lumen wall 404. An incision 406 is made in lumen wall 404 to allow a surgeon to perform a procedure such as, for example, placing a graft, or any other suitable procedure.

To create a bloodless operating field for the surgeon, plug apparatus 400 is inserted into incision 406. Plug apparatus 400 includes a balloon portion 410, first lumen 412 and second lumen 414. First lumen 412 is connected to distal portion 418 of balloon portion 410. Second lumen 414 is connected to proximal portion 416 of balloon portion 410, and is also coaxial with first lumen 412, and is configured to slide over the first lumen. Balloon portion 410 is inserted into lumen 402 such that both first lumen 412 and second lumen 414 are partially inserted into lumen 402. Second lumen 414 may then by pushed in direction 420, forcing proximal portion 416 to fold back towards distal portion 418 such that balloon portion 410 creates a cone-like shape 430. Cone-like shape 430 may then be pulled towards lumen wall 404 to create a hemostatic seal around incision 406. The surgeon may then use suction to clear proximal portion 416 of the cone-like shape of any blood to reveal a bloodless operating field.

Figure 18A:
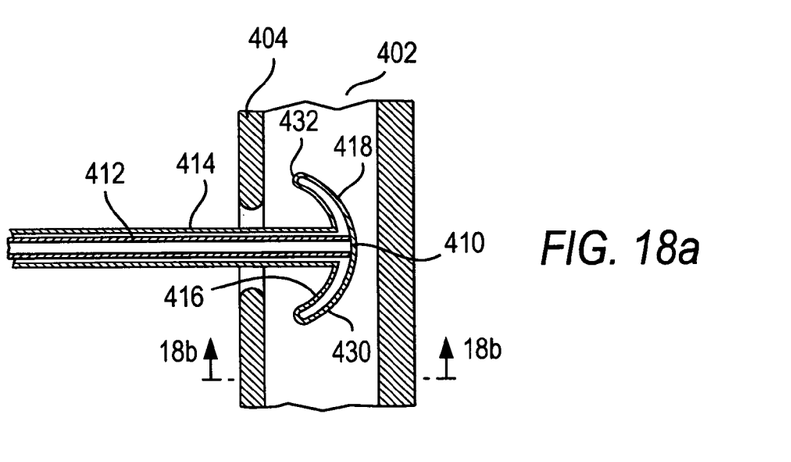
FIG. 18a is a simplified sectional view of the procedure and related apparatus of FIG. 17 in a later stage of the procedure in accordance with the present invention.
Figure 18B:
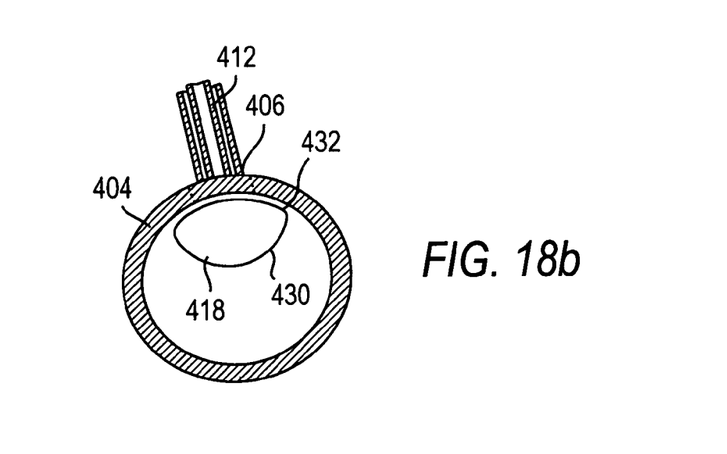

FIG. 18a shows cone-like shape 430 created from balloon structure 410. Cone-like shape 410 creates a hemostatic seal around incision 406 by pulling the structure against the lumen wall. In one embodiment, the diameter of balloon structure 410, which may be an edge of cone-like shape 430 may include a contour 432 that is configured to match the inner contour of lumen wall 404 (shown in FIG. 18b). Contour 432 may be configured to enhance the seal of apparatus 400 with lumen wall 404. A contoured structure may require less force to create a seal between plug apparatus 400 and lumen wall 404. Cone-like shape 430 is configured such that contour 432 is larger than incision 406. In one embodiment, contour 432 extends beyond incision 406 such that a surgeon may suture lumen wall 404 in the region enclosed by contour 432.

After completion of the procedure, plug apparatus 400 may be removed from lumen 402 by pulling second lumen 414 in the direction opposite direction 420 with respect to first lumen 412 such that the cone-like shape reverts to a balloon like shape. Pulling second lumen 414 further may cinch balloon 410 and ease the removal of plug apparatus 400 from lumen 402. First lumen 412 and second lumen 414 may also be twisted relative to each other to reduce the profile of plug apparatus 400. In one embodiment, first lumen 412 and second lumen 414 may also be twisted relative to each other while balloon structure 410 is still in cone-like shape 430 to reduce the profile of the cone-like shape and remove plug apparatus 400 from lumen 402.

Figure 19:
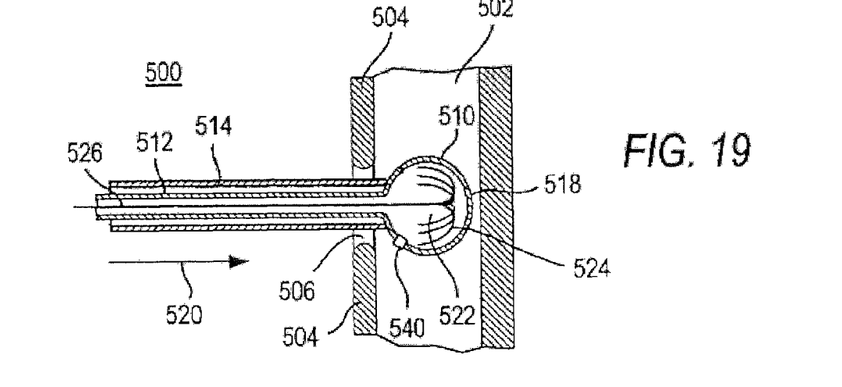
FIG. 19 is a simplified sectional view of the procedure and related apparatus of FIG. 17 with an additional component in accordance with the present invention.

FIG. 19 shows an alternative embodiment of this plug apparatus. Plug apparatus 500 is configured to be used in lumen 502, which includes lumen wall 504 and incision 506. Plug apparatus 500 includes balloon portion 510 such that first lumen 512 is connected to distal portion 518 of balloon portion 510, and second lumen 514 is not connected to any portion of balloon portion 510. Second lumen 514 is coaxial to first lumen 512, and is configured to be slidably placed over first lumen 512. Plug apparatus 500 may also include an internal frame 522. Internal frame 522 may include expansion portion 524 and wire portion 526. Internal frame 522 may be configured to be placed into balloon portion 510 through first lumen 512. Wire 526 may remain accessible outside first lumen 512 to hold internal frame 522 within balloon 510. The internal frame may be shaped to add strength and rigidity to the balloon portion to reinforce the balloon portion against blood pressure inside the lumen, such as the aorta. Internal frame 522 may be shaped like an umbrella frame, or any other suitable shape. Internal frame 522 may include a mesh portion.

Plug apparatus 500 is inserted into incision 506 until balloon portion 510 is entirely within lumen 502. Internal frame 522 may then be threaded through first lumen 512 and into balloon portion 110 such that expansion portion 524 may expand into the balloon portion. In one embodiment, internal frame 522 may be, for example, nitinol wire, or any other material with suitable properties. In one embodiment, internal frame 522 may be a material with superelastic properties, which may allow the internal frame to collapse to fit through first lumen 512 before expanding in balloon portion 510.

Figure 20A:
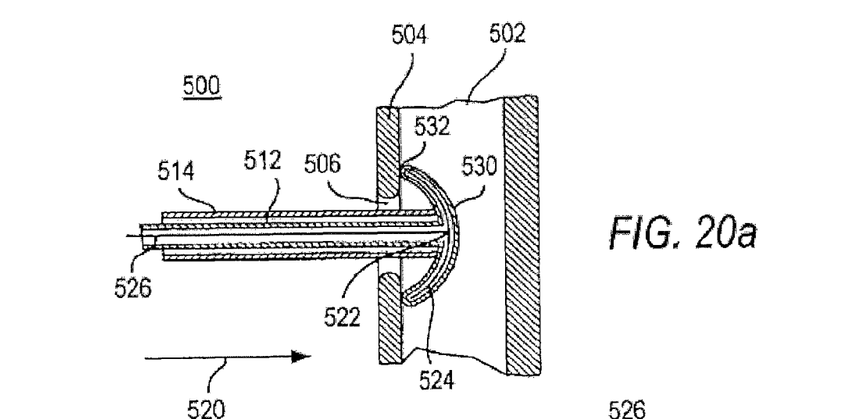
FIG. 20a is a simplified sectional view of the procedure and related apparatus of FIG. 19 in a later stage of the procedure in accordance with the present invention.
Figure 20B:
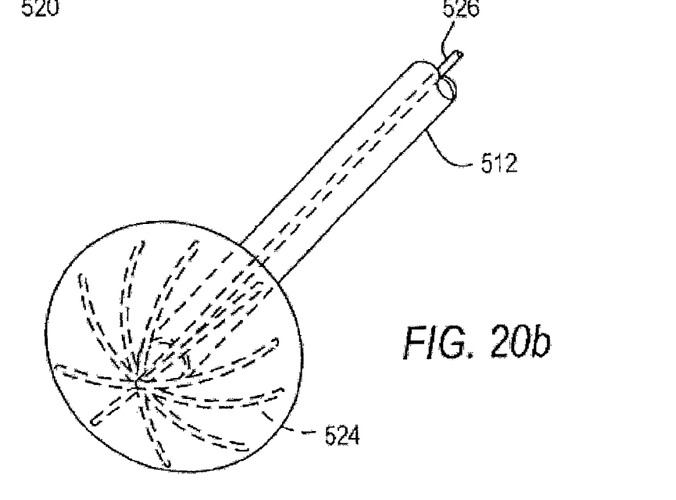
FIG. 20b is a simplified perspective view of the apparatus of FIG. 20a in a different perspective in accordance with the present invention.

To create a bloodless region, the surgeon may hold internal frame 512 while pushing second lumen 514 against balloon portion 510 in direction 520 to force the balloon portion into a cone-like shape 530, as shown in FIG. 20a. The combination of internal frame 522 and second lumen 514 may then be pulled in the direction opposite direction 520 until the edge of cone-like shape 530 is against lumen wall 504. The combination of second lumen 514 and internal frame 522 may resemble an umbrella, as shown in FIG. 20b. In one embodiment, the base of cone-like shape 530 may include contour 532 that is configured to match the inner contour of lumen wall 504. Contour 532 may be configured to enhance the hemostatic seal of apparatus 500 with lumen wall 504. A contoured structure may require less force to create a seal between plug apparatus 500 and lumen wall 504. Cone-like shape 530 is configured such that contour 532 is larger than incision 506. In one embodiment, contour 532 extends beyond incision 506 such that a surgeon may suture lumen wall 504 in the region enclosed by contour 532.

After completion of the procedure, plug apparatus 500 may be removed from lumen 502 by pulling second lumen 514 in the direction opposite direction 520 with respect to first lumen 512 such that the cone-like shape reverts to a balloon like shape. Once balloon portion 510 has regained its original shape, internal frame 522 may be pulled in the direction opposite direction 520 to collapse expansion portion 524 so that it may fit through first lumen 512. Once internal frame 522 has been removed from balloon portion 510, plug apparatus 500 may be removed from lumen 502 through incision 506.

In one embodiment, balloon portion 510 may include a balloon inflation port 540 which may be used to inflate and deflate the balloon. In one embodiment, balloon inflation port 540 may be located on the outer periphery of balloon portion 510 (FIG. 19). In one embodiment, the balloon inflation port may be located at the junction of first lumen 512 and balloon portion 510. In one embodiment, a vacuum source may be applied to port 540 such that balloon portion 510 may deflate and wrap down tightly to internal frame 522. This may further increase the rigidity of cone-like shape 530. Once balloon portion 510 has been deflated to form cone-like shape 530, the surgeon may proceed to pull the cone-like shape against lumen wall 504 to create a seal. When the surgeon has finished working on the bloodless region created by the apparatus, pressure may be reapplied to the balloon portion through port 540 to inflate the balloon portion and allow internal frame 522 and balloon portion 510 to be removed from lumen 502.

Figure 21:
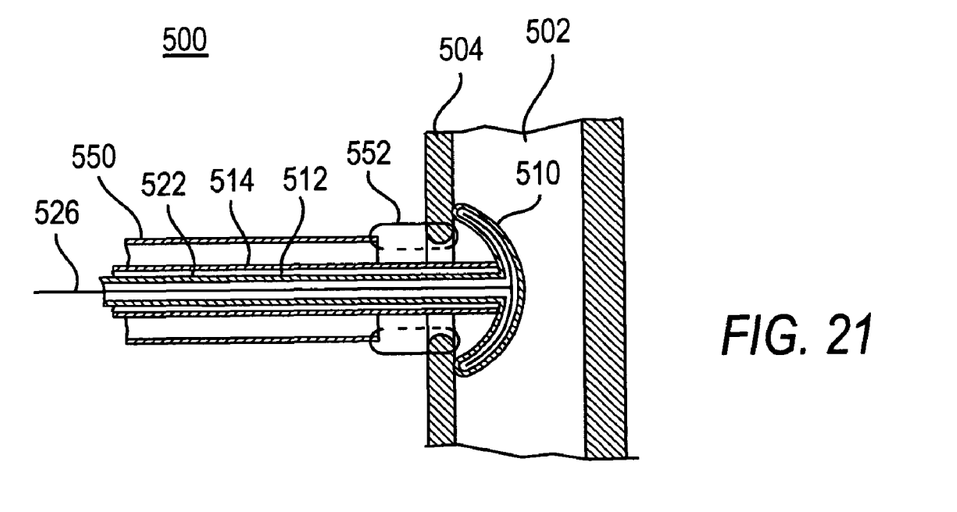
FIG. 21 is a simplified sectional view of the procedure and related apparatus of FIG. 20a in a still later stage of the procedure in accordance with the present invention.

Plug apparatus 500 may be introduced to the anastomotic site through the center of graft lumen 550, which may be configured to be sutured to lumen 502. FIG. 21 shows apparatus 500 introduced through the center of graft lumen 550, which is attached to lumen wall 504 by sutures 552. Once sutures 552 are placed, they may be cinched tight, after which plug apparatus 500 may be removed from the anastomosis site through the inner diameter of graft lumen 550. Alternatively, plug apparatus 500 may be removed from the anastomosis site before sutures 552 are cinched. As shown in FIG. 21, if plug apparatus 500 is introduced through graft lumen 550, first lumen 512, second lumen 514 and wire 526 may be configured to be longer than graft lumen 550 so that a surgeon may grasp plug apparatus 500 to remove it through the proximal end of the graft lumen. In one embodiment, second lumen 514 may be configured to be free of sharp edges and other traumatic features, so as to avoid trauma to graft lumen 550 as plug apparatus 500 is removed. In one embodiment, balloon portion 510, first lumen 512 and frame 522 may be removed from the anastomosis site through second lumen 514. Once all components but second lumen 514 have been removed, second lumen 514 may be removed.

Figure 22:
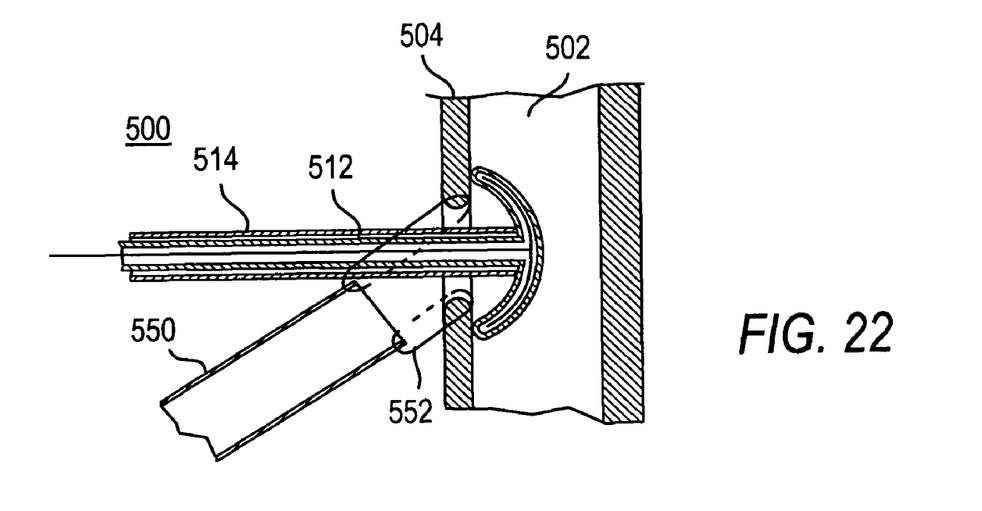
FIG. 22 is a simplified sectional view of the procedure and related apparatus of FIG. 20a in an alternate configuration of a later stage of the procedure in accordance with the present invention.

In embodiments where apparatus 500 does not pass through graft lumen 550, plug apparatus 500 may be removed from the anastomosis site between sutures 552 which connect lumen wall 504 to graft lumen 550. FIG. 22 shows graft lumen 550 attached to lumen 502 with loose sutures 552. Once the sutures are in place and only require cinching to complete the anastomosis, plug apparatus 500 may be removed. In an alternative embodiment, plug apparatus 500 may be introduced and withdrawn through a separate incision made in lumen 502. After completion of the anastomosis and removal of plug apparatus 500, the separate incision may be closed using standard surgical techniques such as, for example, purse-strings, or any other suitable technique.

Advantages of this particular apparatus include eliminating patient blood loss, eliminating the need to clamp lumen 502, no foreign material left behind, minimization of the compressive force against lumen wall 504 to create a hemostatic seal, and the apparatus is adaptable with current surgical techniques, as well as other advantages.

It will be appreciated that features illustrated in connection with one hemostatic seal apparatus according to the invention may be present in some embodiments of other plug apparatus. In particular, it will be appreciated that all sealing apparatus may include the feature of being reconfigurable from a first, expanded configuration to a second, collapsed configuration.

It will be understood that the foregoing is only illustrative of the principles of the invention, and that various modifications can be made by those skilled in the art without departing from the scope and spirit of the invention. For example, the order of some steps in the procedures that have been described are not critical and can be changed if desired.

What is claimed is:

1. Apparatus for temporarily and hemostatically sealing an opening in a side wall of a tubular lumen to form a bloodless region for a surgical operation, comprising:
    a plug having a surface adapted to press against an inner surface of the lumen in a use condition and having a periphery and at least one rib positioned inside the periphery;
    a primary shaft connected to the plug, the primary shaft being configured to extend in a substantially parallel manner with respect to a longitudinal axis of the lumen in the use condition; and
    a first side shaft coupled to the primary shaft and having a first arm, and a second side shaft coupled to the primary shaft and having a second arm, the first and second arms being disposed in a plane and defining a space therebetween, the first and second arms adapted to press against an outer surface of the lumen in the use condition,
    wherein in the use condition, when a hemostatic seal is created, the plug intersects the plane and a projection of the plug onto the plane from a direction normal to the plane is disposed entirely within the space.

2. The apparatus of claim 1 wherein the plug is reconfigurable in use from a first configuration to a second configuration, the surface being collapsed in the first configuration and the surface being stiff in the second configuration.

3. The apparatus of claim 2 wherein the plug comprises a thin-walled portion.

4. The apparatus of claim 3 wherein the thin-walled portion is made from stainless steel.

5. The apparatus of claim 3 wherein the thin-walled portion is made from nitinol.

6. The apparatus of claim 2 wherein the apparatus is adapted to be placed in the lumen through the opening.

7. The apparatus of claim 2 wherein the apparatus is adapted to be placed in the lumen through a second opening.

8. The apparatus of claim 2 wherein in the use condition the at least one rib is configured to rest against the lumen wall such that the lumen wall is visibly accessible.

9. The apparatus of claim 8 wherein the entire lumen wall is visibly accessible.

10. The apparatus of claim 2 wherein the portion of the plug that is in contact with the lumen wall in the use condition is configured to be larger than the opening.

11. The apparatus of claim 1 wherein the first and second arms are configured to enhance the seal between the plug and the lumen.

12. The apparatus of claim 11 wherein in the use condition the first and second arms are configured to press against the lumen wall to increase the pressure between the plug and the inner surface of the lumen.

13. The apparatus of claim 1 wherein the first and second side shafts are movably coupled to the primary shaft.

14. The apparatus of claim 13 wherein the primary shaft and at least one of the first and second side shafts include locking portions configured to maintain the position of the primary shaft relative to the at least one of the first and second side shafts.

15. The apparatus of claim 14 wherein the locking portions comprise magnetic material.

16. The apparatus of claim 14 wherein the locking portions comprise teeth.

17. The apparatus of claim 1 wherein the plug is adapted to be inserted into the lumen and positioned against the inner surface of the lumen around the opening in the use condition to create a hemostatic seal proximal to a surgical operation site located outside the periphery of the plug.

* * * * *